United States Patent [19]
Berry, Jr.

[11] Patent Number: 5,441,709
[45] Date of Patent: Aug. 15, 1995

[54] SELECTIVE HOLDER DESIGN AND POSITIONING PATTERN

[75] Inventor: Bernie B. Berry, Jr., Indianapolis, Ind.

[73] Assignee: Carr Metal Products, Inc., Indianapolis, Ind.

[21] Appl. No.: 250,298

[22] Filed: May 27, 1994

[51] Int. Cl.$^6$ .............................. A61L 2/00; A61L 2/26
[52] U.S. Cl. ...................... 422/297; 206/370; 206/438; 206/480; 211/184; 220/553; 422/292; 422/300
[58] Field of Search .............. 422/292, 294, 300; 206/363, 369, 370, 438, 480; 211/184, 126; 220/553, 527, 529, 532; 24/704.1, 453, 697.1

[56] References Cited

U.S. PATENT DOCUMENTS

| | | | |
|---|---|---|---|
| 3,255,987 | 6/1966 | Gatch | 211/184 X |
| 3,285,409 | 11/1966 | Loran. | |
| 3,634,937 | 1/1972 | Green. | |
| 4,135,868 | 1/1979 | Schainholz | 422/300 X |
| 4,191,291 | 3/1980 | Brown | 206/369 |
| 4,253,830 | 3/1981 | Kazen et al. | 433/77 |
| 4,262,799 | 4/1981 | Perrett | 422/300 X |
| 4,353,694 | 10/1982 | Pelerin | 433/77 |
| 4,541,992 | 9/1985 | Jerge et al. | 422/300 |
| 4,643,303 | 2/1987 | Arp et al. | 206/370 |
| 4,762,688 | 8/1988 | Berry, Jr. | 422/310 |
| 4,774,063 | 9/1988 | Runnells | 422/297 |
| 4,798,292 | 1/1989 | Hauze | 206/439 |
| 4,854,475 | 8/1989 | Riihimaki et al. | 220/337 |
| 4,959,199 | 9/1990 | Brewer | 422/300 |
| 5,084,251 | 1/1992 | Thomas | 422/300 |
| 5,098,676 | 3/1992 | Brooks, Jr. | 422/292 |

Primary Examiner—Robert J. Warden
Assistant Examiner—Krisanne M. Thornton
Attorney, Agent, or Firm—Woodard, Emhardt, Naughton, Moriarty & McNett

[57] ABSTRACT

An autoclave tray for the sterilization of medical and/or dental instruments, equipment and appliances includes an autoclave tray which is configured with a uniform row and column pattern of crossed-slot sterilant apertures each of which have a geometric center, the pattern being generally uniform in its overall spacing between such geometric centers. Selectively installed in selected ones of the sterilant apertures are instrument holders which begin as extruded lengths of material which are then cut to the desired length and shaped with appropriate relief for the receipt of the items to be autoclaved. The holders are loaded into selected sterilant apertures by pressing an enlarged base portion of the holders into and through the sterilant apertures. By the use of the crossed-slot apertures the holders can be arranged either vertically or horizontally in a top plan orientation or may actually be used at right angles to each other allowing items to be autoclaved to be installed diagonally. The dimensioning of the holders relative to the dimensioning of the sterilant apertures results in sterilant openings being disposed on either side of the installed holder, these openings coming from the sterilant apertures which are actually used to receive the holder.

18 Claims, 4 Drawing Sheets

SELECTIVE HOLDER DESIGN AND POSITIONING PATTERN

BACKGROUND OF THE INVENTION

The present invention relates in general to autoclave trays, cases and enclosures wherein various holders, brackets, racks and clamps are used to secure and retain a variety of surgical and/or dental components, instruments and related medical apparata. More specifically the present invention relates to the selective and arbitrary customizing of holders for such components, instruments and related apparata as well as the selective arranging of the holders into the receiving tray.

Within the field of autoclave trays, cases and enclosures there are numerous design approaches which have been used over the years to try and receive and secure in place the particular items which need to be sterilized. One category of design approach involves the use of separate racks which actually receive the items and these racks are then positioned in some type of tray or enclosure for the purposes of storage and sterilizing. On occasion the lid portion of the case or enclosure is used to clamp down on the items or onto the rack or both as the means to keep the items stationary and not allow them to move around or shift in position during handling and autoclaving. A representative sampling of patents involving this design approach is provided by the following listed references:

| Pat. No. | Patentee | Issue Date |
| --- | --- | --- |
| 4,774,063 | Runnells | Sep. 27, 1988 |
| 4,959,199 | Brewer | Sep. 25, 1990 |
| 4,643,303 | Arp et al. | Feb. 17 1987 |
| 5,084,251 | Thomas | Jan. 28, 1992 |
| 4,854,475 | Riihimaki, et al. | Aug. 8, 1989 |
| 3,634,937 | Green | Jan. 18, 1972 |
| 3,285,409 | Loran | Nov. 15, 1966 |

Another category of design approach involves the use of a plurality of holders whose positions are essentially fixed in the tray. The components, instruments and related apparata are then loaded into these fixed holders for autoclaving and safe storage after autoclaving. A representative sampling of patents following this second design approach category is provided by the following listed patent references:

| Pat. No. | Patentee | Issue Date |
| --- | --- | --- |
| 4,191,291 | Brown | Mar. 4, 1980 |
| 4,762,688 | Berry | Aug. 9, 1988 |
| 4,541,992 | Jerge, et al. | Sep. 17, 1985 |
| 4,253,830 | Kazen | Mar. 3, 1981 |

As might be expected there is on occasion a patent reference which might arguably fit in both categories and from time to time patent references that might not easily fit into any general category. A representative sampling of these types of patents is provided by the following listed patent references:

| Pat. No. | Patentee | Issue Date |
| --- | --- | --- |
| 4,798,292 | Hauze | Jan. 17, 1989 |
| 4,353,694 | Pelerin | Oct. 12, 1982 |
| 5,098,676 | Brooks, Jr. | Mar. 24, 1992 |

One of the drawbacks with almost any type of autoclave tray, case or enclosure when the style of the holders, brackets, racks and clamps are fixed or limited and when their positioning within the tray, case or enclosure is fixed or limited, is the lack of versatility and opportunity for customizing. With fixed designs there are no provisions made to allow for design freedom nor to enable the handling of unique and unusual items. Suppose a physician or dentist has a special instrument, possibly a custom made item for some unique procedure, how can it be handled by fixed-design holders and fixed positioning trays?

When trying to offer greater design freedom and flexibility there are other shortcomings which may be introduced that actually detract from the overall suitability of the new design. Consider for example the device disclosed in U.S. Pat. No. 5,098,676 wherein a fingermat is styled for an autoclave tray. Some of the key features to note regarding this reference include the fact that the fingermat has a size which completely covers and fills the bottom or floor of the corresponding tray. This particular design feature creates two other problems including first that any sterilant apertures which are formed or machined into the tray floor would initially be covered over by the fingermat. Secondly, there are potentially large areas of the fingermat which may in fact not be needed to receive and retain specific instruments or equipment and thus there is a cost inefficiency since the unused fingermat material will be wasted.

In order to try and solve the problem of covering or blocking sterilant apertures, the fingermat as disclosed in the '676 patent is provided with a plurality of flow apertures (34) and a total of 15 are illustrated. However, this pattern is predetermined and wherever flow apertures are located, the mat fingers must be removed and thus there is a corresponding loss of some of the design freedom. Further, since current design wisdom focuses on trying to create the maximum flow through and circulation of sterilant, it is desired to have more sterilant apertures rather than fewer. Obviously, the more that are introduced into the fingermat the fewer number of fingers and thus the less design freedom which is provided for arranging the items to be autoclaved.

Another reference to be considered in the sense of flexibility and design freedom is U.S. Pat. No. 4,762,688 wherein an autoclave tray is disclosed that uses a synthetic material holder to securely retain the medical instruments and components, while the extruded holder offers some design freedom because it can be customized by cutting and shaping, the receiving slots in the tray have fixed locations. The nomenclature on the top surface of the tray (see FIG. 2 of the '688 patent) indicates that the particular tray is intended for a predetermined and specific grouping of items, possibly a package that would correspond to one specific surgical procedure such as a total hip replacement. One of the features of the '688 patent is the use of a keyhole shaped entry aperture at one end of each receiving slot so that the base portion of the holder can slide into position and thereafter seat securely. It is also possible to remove the extruded holder by reversing the sequence of insertion steps. The holder base is continuous and it is relatively wide in comparison of the width of the receiving slot which is also continuous from the entry aperture to the closed end.

While the holder design flexibility and the mounting technique are clearly desirable features of this invention, the fixed layout and mounting pattern preclude having any design freedom as far as customizing the tray for a particular grouping of items in a particular pattern or arrangement. After studying and learning from the limitations of earlier designs, the present invention was conceived. The objective was to try and create an autoclave tray and holder combination which provides some of the desirable aspects of earlier concepts, but with greater flexibility for special layouts and customized arrangements, all at lower cost with higher reliability and all in a unique and unobvious package. The first step for this design evolution was to specifically target the key features and then see if it would be possible to provide all of those features without introducing any new shortcomings or problems.

The result of this design effort is the present invention which is disclosed herein. The design of the tray includes a uniform pattern of spaced sterilant apertures disposed throughout the surface of the tray so that there is an ample flow through of sterilant. These sterilant apertures double as receiving apertures for holders which are, in the preferred embodiment, flexible, silicone extrusions. These extruded holders can be provided in virtually any length and cut or shaped in virtually any manner with holes, notches, slots, etc. for receiving and holding some portion of a medical or dental instrument or component.

The tray layout can be predetermined and the holders created and installed by the manufacturer or the tray can be customized on site. The holder styles can be predetermined, standard holders can be offered, or the extruded holders can be customized on site. The tray and holder are compatibly configured such that the holder can be pushed into the tray apertures. However, once the holder is installed in the selected tray apertures, it will remain in position due to its own material properties including hardness and due in part to the nature of the interference fit between the base of the holder and the tray apertures. While removal of the holder from the aperture will likely damage the base of the holder, the extruded holders are relatively inexpensive and a new holder can be readily provided, modified as necessary and installed.

Each of these aspects of the present invention will be described in greater detail hereinafter, including a discussion of some of the unique benefits of the present design which would not be expected based upon earlier designs and current design concepts.

SUMMARY OF THE INVENTION

A combination of an autoclave tray and a plurality of instrument holders according to one embodiment of the present invention includes an autoclave tray which is designed to receive medical-type items. The tray is arranged with a plurality of sterilant apertures each having a geometric center and which are disposed in a pattern with generally uniform spacing between the geometric centers. A plurality of extruded holders are assembled into the tray by using selected ones of the plurality of sterilant apertures in order to receive an enlarged base portion of each holder.

One object of the present invention is to provide an improved autoclave tray and holder combination.

Related objects and advantages of the present invention will be apparent from the following description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
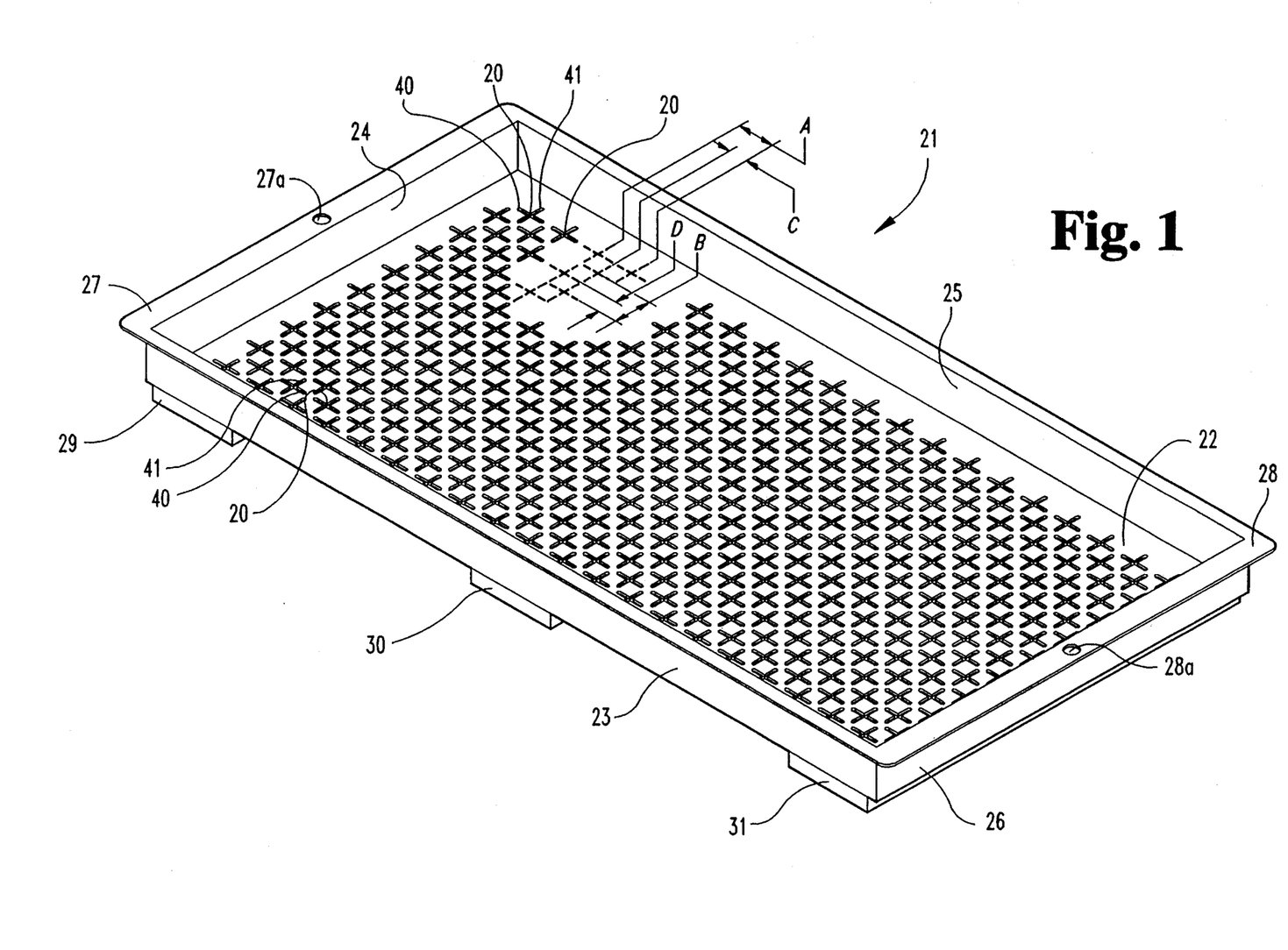
FIG. 1 is a perspective view of an autoclave tray having a specific sterilant aperture pattern according to a typical embodiment of the present invention.
Figure 2:
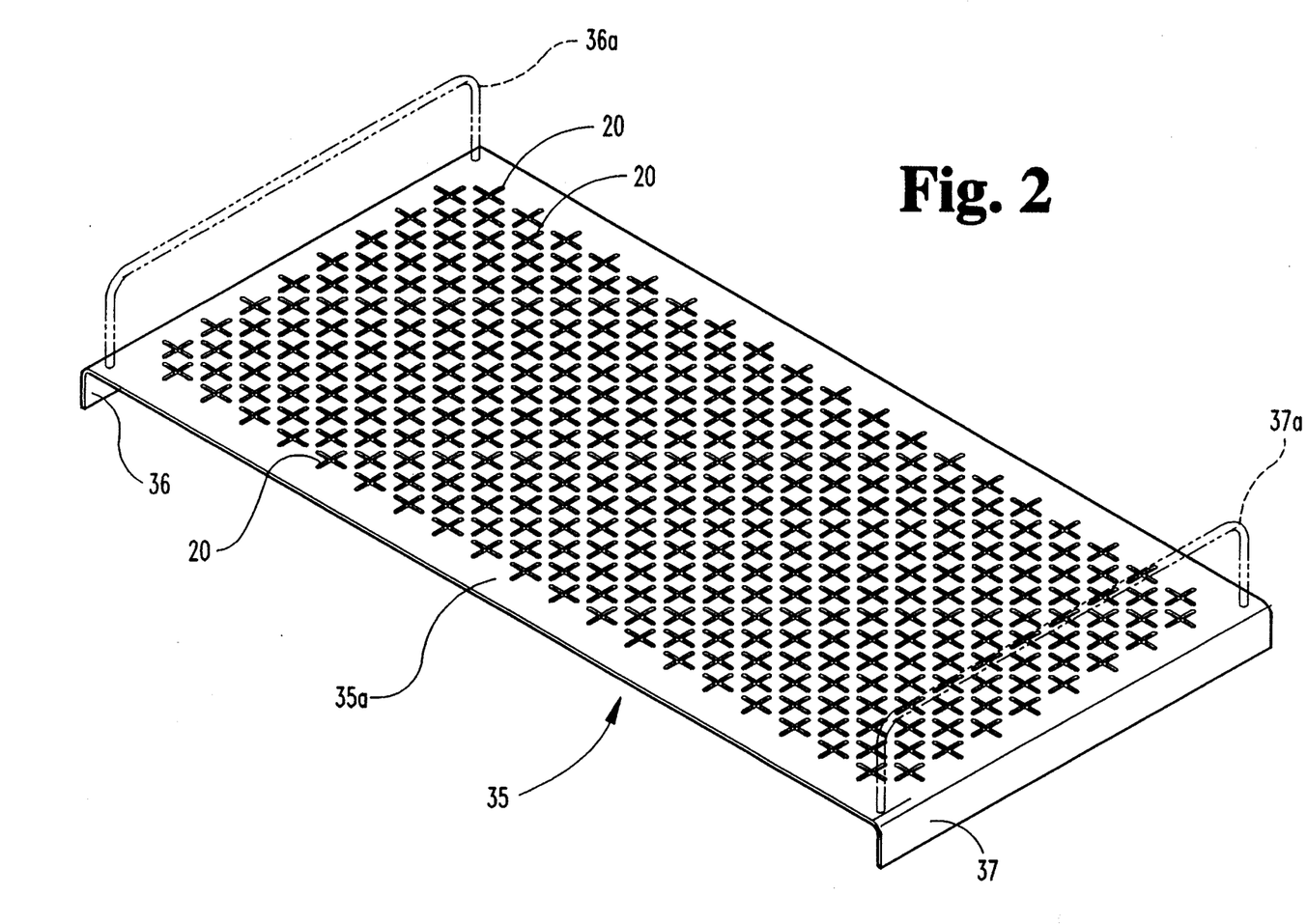
FIG. 2 is a perspective view of an autoclave shelf having a specific aperture pattern according to a typical embodiment of the present invention.

Referring to FIGS. 1 and 2, two of several possible autoclave tray designs according to the present invention are illustrated. The key feature of each tray is the size, shape, spacing and edge definition of the crossed-slot sterilant apertures 20. Although referred to as "sterilant apertures", which is of course true, selected ones of these apertures will actually be used to receive and retain extruded silicone holders which are designed to hold medical and dental instruments and components (see FIG. 7).

In FIG. 1, tray 21 has a recessed base panel 22, four surrounding sidewalls 23–26, side flanges 27 and 28 and spacer feet 29–31. The spacer feet 29–31 may extend the entire width of the base panel 22 or may be arranged as corner feet in which case the center spacer foot 30 would be eliminated. As will be understood, when a holder (see FIGS. 3 and 4) is inserted into selected ones of apertures 20, the lower portion (base) of the holder extends through the panel thickness of recessed base panel 22. While the lower portion of the holders may provide their own clearance and thus serve as feet, there will still be some type of clearance on the back or underside. Ideally the spacer feet 29–31, whether used as illustrated or as corner feet, will be slightly higher (deeper) than the height of the lower portion of the holders so that the inserted portion of each holder will not interfere with whatever countertop, table or shelf on which tray 21 may be placed. The flanges 27 and 28 are used to handling of tray 21 and tray 21 may be used with an enclosing lid. If a lid is used the two flanges may each be fitted with a clearance hole 27a and 28a for the assembly of a lid-securing latch. The preferred material for tray 21 is metal, either a suitable aluminum alloy or steel. However, certain grades of plastic can be used.

Referring now to FIG. 2, tray 35 has a substantially flat main panel 35a formed with depending side flanges 36 and 37 which serve as support feet. The vertical height of the flanges is sufficient to provide clearance between the inserted portion of any holder and the top surface of whatever countertop, table or shelf is used to receive the tray 35. For lifting and transport, tray 35 may include side handles 36a and 37a and the tray may be used in the form illustrated or may be received within an enclosure, case or cassette and thereby serve as a lift-out shelf.

Since the focus of the design of trays 21 and 35 resides in the sterilant apertures 20 and their overall pattern, those details will now be described. First, each of the sterilant apertures 20 are intended to be virtually identical and configured as if two slots are crossed at a right angle to each other. Each of the apertures 20 include a first oblong slot 40 which measures approximately 0.75 inches (1.9 cm) in length and a crossing slot 41 which also measures approximately 0.75 inches (1.9 cm) in length. The approximate width of each slot is 0.093 inches (2.36 mm) and each slot is centered on a corresponding centerline. These centerlines provide the dimension lines used for dimensions "A", "B", "C", and "D". The apertures are arranged as if in a uniform matrix of columns and rows (one way to describe the pattern) when looking down on the tray or shelf and this arrangement of columns and rows is in fact arranged with an offset or staggered pattern. Each slot crosses the other slot at the corresponding centers and the geometric center of this slot intersection is the geometric center of the aperture. It is also appropriate to look at the staggered pattern of apertures in the rows and columns as comprising a uniform and repeating four-corners diamond pattern (see FIG. 8).

The centerline spacing (dimension "A") between each column of the same row is approximately 1.00 inch (2.54 cm) and the centerline spacing (dimension "B") between each row of the same column is likewise approximately 1.00 inches (2.54 cm). These dimensions are taken between the geometric centers of the apertures. Due to the staggered arrangement, the spacing (dimension "C") between adjacent columns without regard to the row is approximately 0.50 inches (1.27 cm) and the spacing (dimension "D") between adjacent rows without regard to the column is approximately 0.50 inches (1.27 cm). The ends of each slot 40 and 41 are formed with a full radius. While these dimensions are identified in FIG. 1, they are also included in FIGS. 7 and 8 whereat it may be easier to appreciate how this pattern of sterilant apertures is arranged and how it is used as part of the present invention.

Figure 3:
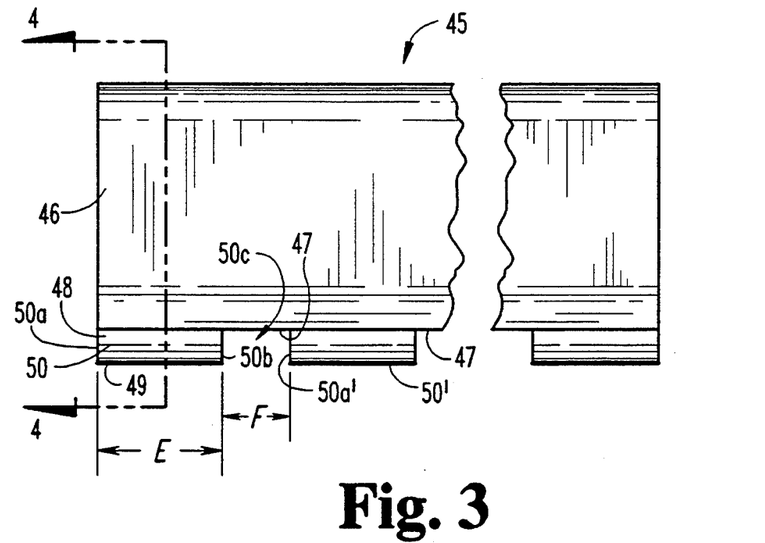
FIG. 3 is a partial, front elevational view of an extruded holder which is designed so as to be installed within selected apertures of either the FIG. 1 or FIG. 2 autoclave structures.
Figure 4:
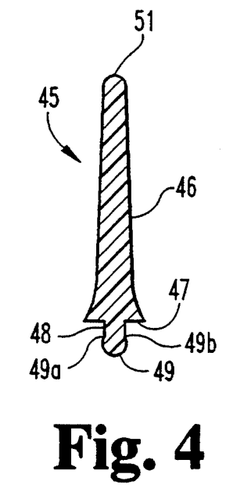
FIG. 4 is a side elevational view in full section of the FIG. 3 holder as viewed along line 4—4 in FIG. 3.
Figures 4A, 5, 6:
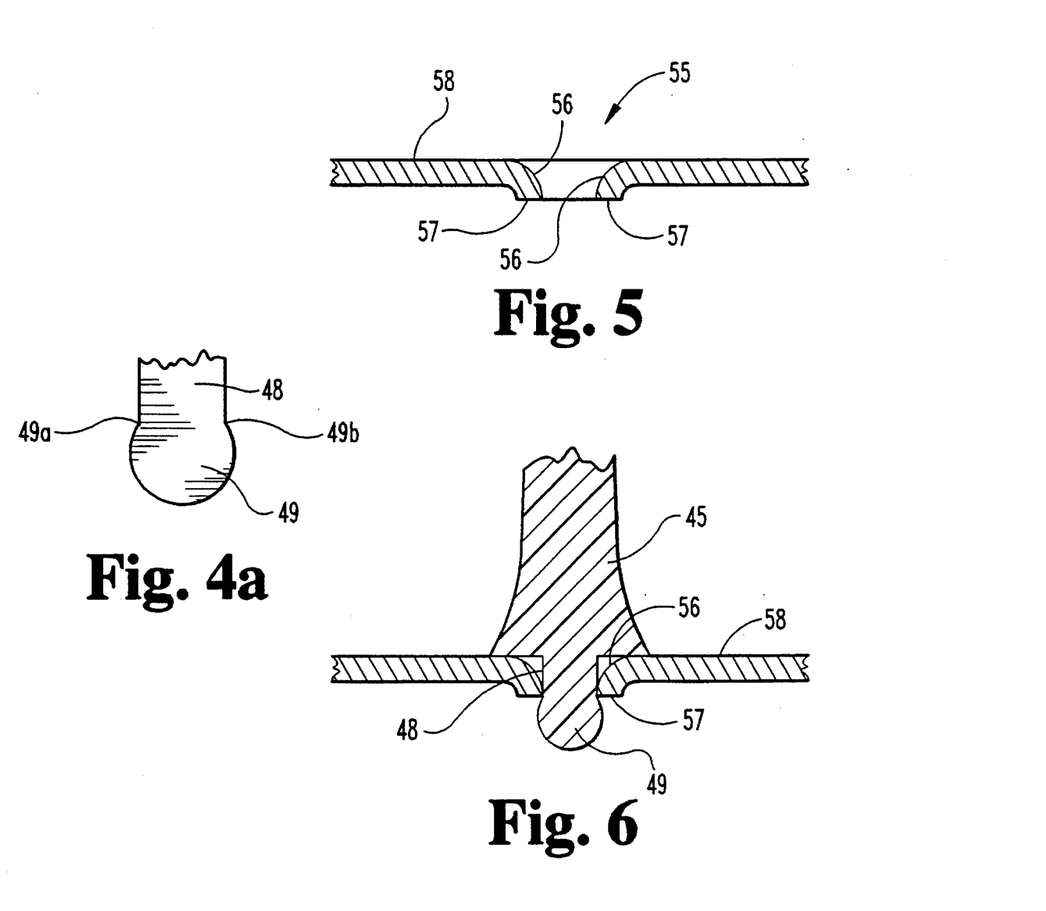
FIG. 4A is a partial, enlarged detail, side elevational view of the lower portion of the FIG. 3 holder.
FIG. 5 is a front elevational view in full section of a tray panel illustrating a portion of one of the tray/shelf apertures according to the present invention.
FIG. 6 is a partial, front elevational view in full section of the FIG. 5 aperture as receiving a portion of a FIG. 3 holder in accordance with the present invention.

Referring to FIGS. 3, 4 and 4A, holder 45 is illustrated first as a partial, front elevational view (FIG. 3) and then as a side or end elevational view in full section (FIG. 4). FIG. 4A provides an enlarged detail of the lower portion of the holder. Holder 45 is extruded out of silicone (rubber) and is flexible yet still somewhat rigid so as to hold its form and provide suitable support and retention for whatever medical or dental items might be loaded into the arrangement of holders for the purposes of autoclaving and then subsequent storage. The holders can be cut and shaped fairly easily thereby allowing the physician or dentist the option of customizing the holders to be able to receive whatever items and in whatever manner is desired. Some of the holders to be used in the tray can be standardized with a slotted pattern of receiving holes or some other shape. It is also envisioned that the end user may actually specify as part of a particular tray order how the holders are to be configured and how they will be arranged in the tray. All three options might be present in any one tray assembly.

An end user might know that some portion of the tray will always be used for one grouping of items and the required holders can be arranged by the manufacturer in advance and installed in the tray according to the specific design specified. The end user might also order some holders with a standard slot and/or hole configuration knowing that from time to time certain standard items will be added to the autoclave tray and that these items can be secured in the desired manner by the standard (preconfigured) holders. Finally, the end user may order a length or lengths of blank extruded holders without any customizing or shaping. The end user can then cut the extruded length to a shorter desired length and then create the relief and shapes which are required to receive and retain some unique or specialized item. These "blank" extrusions can also be used as replacements in the event a pre-customized or standardized holder is damaged. The end user merely has to cut and shape the blank holder to the desired style.

Each holder is extruded with a tapered main body 46, a substantially flat bottom surface 47, an undercut slot web 48 and an enlarged, ball-shaped tang 49. Tang 49 has a generally circular shape in lateral cross section but is extruded in length so it is actually cylindrical or part-cylindrical due to the presence of web 48. The web 48 and tang 49, as contrasted to the main body, are not continuous in length. The web and tang are configured (see FIG. 3) in section lengths (dimensions "E") of approximately 0.65 inches (1.65 cm) separated by a space (dimension "F") of approximately 0.35 inches (0.0889 cm). dimensions "E" and "F" are important relative to the dimensions of the sterilant apertures and the pattern spacing. First, the length of each web and tang section 50 is short enough to fit within either slot 40 or slot 41 of anyone aperture. Secondly, the center-to-center spacing of each web and tang section 50 is approximately one inch (2.54 cm) which is the same center-to-center spacing of apertures 20 which are in the same row or in the same column. Each web and tang section 50 has a leading edge 50a which can be thought of as the first portion exiting from the extruder and a trailing edge 50b. The space 50c between each extruded section is defined by the trailing edge 50b of the first section 50 and the leading edge 50a' of the second section 50=.

Each holder measures approximately 1.25 inches (3.175 cm) in body height from surface 47 to the full radius upper tip 51. The maximum width at surface 47 measures approximately 0.312 inches (0.79 cm). Web 48 is approximately 0.105 inches wide (0.267 cm) and approximately 0.08 inches (2.03 mm) high between surface 47 and the opposing upper edges 49a, 49b located at the top of tang 49 (see FIG. 4A). The generally circular shape of tang 49 in lateral cross section measures approximately 0.125 inches (3.18 mm) in diameter. When using a tray with a thickness of something less than 0.08 inches (2.03 mm) the top edges 49a and 49b of the tang will abut up against the back side of the panel that comprises the tray (i.e., the panel receiving the sterilant apertures). Since the aperture slots 40 and 41 are approximately 0.093 inches in width the 0.105 inch web width will cause interference in the fit of the sides of the web within the corresponding slot. This interference fit helps anchor the holder in position in the event the tang abutment would not provide sufficient holding strength. The tightness of the abutment of the tang against the back side or underside of the panel is controlled by the panel thickness. When the panel is thicker than the length of web 48 there will be some degree of an interference fit in an axial direction between the tang 49 and the panel.

The circular (diameter) shape of tang 49 which is the axial leading edge for the insertion of the holder, enables the holder to be more easily inserted into the selected aperture. The holder material also contributes somewhat to the ease of assembly. A further feature of the present invention which contributes to how easily the holder may be installed in the selected aperture is the lip or edge curvature formed in the slots 40 and 41 of each aperture 20. As illustrated in FIG. 5, slot 55 which may correspond to either a slot 40 or a slot 41, has a pair of oppositely disposed, curved slot edges 56 and a shallow lip 57 on the back side or underside of the tray panel 58. The tang will actually abut up against lip 57 as is illustrated in FIG. 6. Web 48 is thus positioned within slot 55 and dimensionally if a 0.063 inch starting panel thickness is formed with a 0.017 lip there will be a stack up of dimensions of approximately 0.080 inches or a line to line fit based upon the axial length of web 48. The particular curvature which is illustrated with regard to slot edges 56 is created by means of a punch and die arrangement where the normal clearance between the punch and the die is increased so as to get this curved slot edge which is illustrated.

Figure 7:
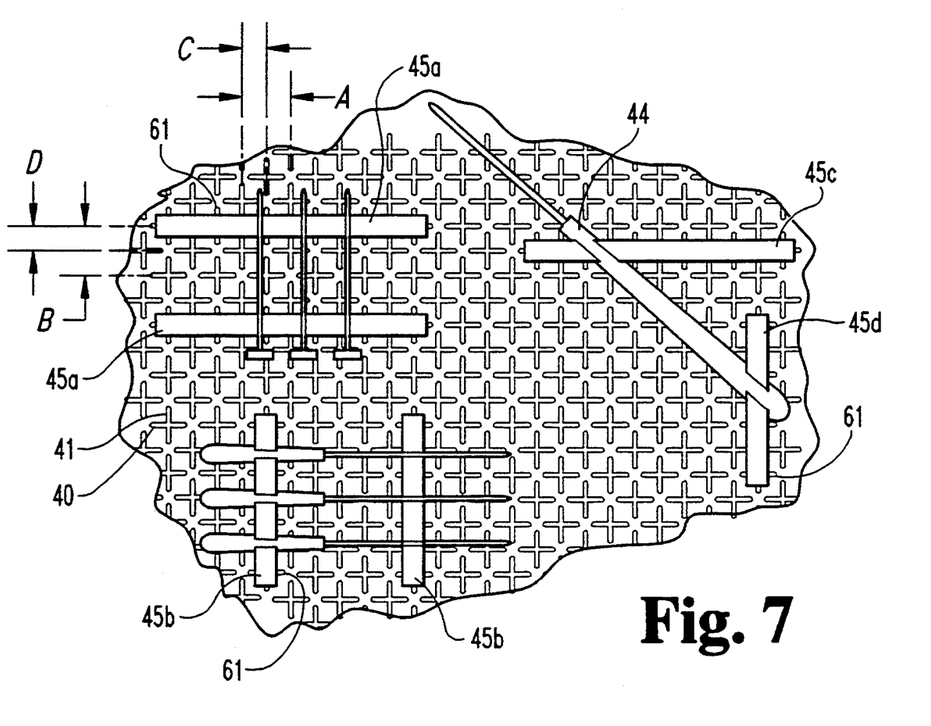
FIG. 7 is a partial top plan view of a tray with an aperture pattern receiving various holders and arranged with medical devices installed within the holders according to the present invention.
Figure 8:
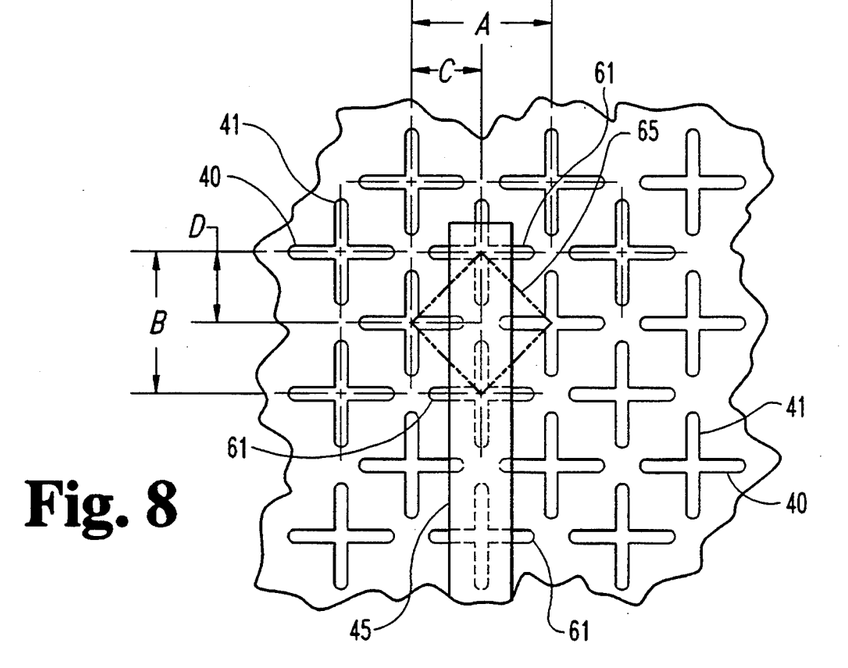
FIG. 8 is a partial, top plan view, slightly enlarged and illustrating the dimensional spacing of the aperture pattern and the dimensional relationships of those apertures relative to the FIG. 3 holder in accordance with the present invention.

One of the features of the present invention is the ability to place the holders in either or both a horizontal (row) direction or a vertical (column) direction, with these directions being based on a top plan view or looking down on the tray as in the arrangement of FIGS. 7 and 8. In FIG. 7 some holders 45a are arranged horizontally using aperture slots 40 and other holders 45b are arranged vertically using aperture slots 41. Representative medical items are installed in the holders which are configured with narrow slots cut in the main body 46 of the holder down through the upper tip 51.

FIG. 7 also illustrates one of the unique features of the present invention, namely the ability to arrange two holders at a right angle to each other and then install an instrument diagonally so as to span the corner created by the two holders. In this particular configuration, holder 45c uses the aperture lots 40 while holder 45d uses aperture slots 41. The handle 44 of the instrument which is only partially illustrated is inserted diagonally so as to cut across the corner formed by the right angle holder pattern.

Another unique feature of the present invention can be appreciated from the FIG. 8 illustration. From the foregoing description it will be appreciated that each slot 40 and 41 is approximately 0.75 inches long and that the maximum width of the holder 45 is approximately 0.312 inches. This leaves an opening 61 of approximately 0.219 inches in length extending beyond the sides of the installed holder regardless of which slot is used to receive the holder. In the FIG. 8 illustration slot 41 is used for the holder 45 and thus the clearance openings 61 come from the ends of the corresponding slot 40. FIG. 8 also illustrates the four-corners diamond pattern for the apertures. The broken line 65 depicts one such diamond pattern.

The present invention provides a very interesting configuration and combination of features. Not only can the sterilant aperture double as apertures to receive and retain the instrument holders, but the holders can be selectively arranged in rows or columns or both with virtually unlimited freedom. The apertures are not dedicated in the sense of being either a sterilant aperture or a holder aperture and any aperture which is not used for a holder will be used for its full area to contribute to the maximum flow of sterilant through the tray and the autoclave enclosure. Uniquely, even the apertures which are used for holders have been dimensioned so as to still provide some sterilant openings on each side of the holder to enhance the sterilization of whatever items are installed in the holders.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A combination comprising:
an autoclave tray for medical components which is arranged with a substantially planar main panel which defines a plurality of crossed-slot sterilant apertures, each sterilant aperture having a geometric center and being positioned in a substantially uniform pattern of staggered rows with substantially uniform spacing between said geometric centers within each row; and
a plurality of integral holder panels which are constructed and arranged to receive said medical components and to assemble into said main panel by using selected ones of said plurality of sterilant apertures, each of said plurality of holder panels having a main body portion positioned on a first side of said main panel, an elongated base portion positioned on a second side of said main panel, said second side being oppositely positioned relative to said first side, and a web portion positioned between said main body portion and said elongated base portion, said web portion being captured by a corresponding one of said crossed-slot sterilant apertures, each elongated base portion including a plurality of spaced-apart insert ribs, the assembly of each holder panel of said plurality into said main panel being achieved by each of said plurality of spaced-apart insert ribs being inserted through a different one of said crossed-slot sterilant apertures.

2. The combination of claim 1 wherein said main body portion has a substantially flat lower surface and said elongated base portion has oppositely disposed upper edges, and wherein said main panel has a thickness which is substantially equal to the distance between the substantially flat surface of said main body portion and the upper edges of said elongated base portion.

3. The combination of claim 2 wherein said elongated base portion has a generally circular shape in lateral section.

4. The combination of claim 1 wherein each crossed-slot sterilant aperture of said plurality includes a first oblong slot having a first centerline axis and crossing at an approximate right angle therewith a second, substantially identical oblong slot having a second centerline axis, the first and second centerline axes intersecting at the geometric center of the corresponding aperture.

5. The combination of claim 1 wherein a first one of said plurality of spaced-apart insert ribs having an elongated length with a leading edge and a trailing edge and the next adjacent spaced-apart insert rib having a substantially equivalent elongated length with a leading edge and a trailing edge, wherein the trailing edge of said first insert rib is spaced apart from the leading edge of said next adjacent insert rib.

6. The combination of claim 5 wherein the length dimension from the leading edge of said first insert rib to the leading edge of said next adjacent insert rib is approximately equal to the distance between geometric centers within each row.

7. A combination comprising:
an autoclave tray for medical components which is arranged with a substantially planar main panel which defines a plurality of crossed-slot sterilant apertures, said plurality of crossed-slot sterilant apertures being arranged in a substantially uniform pattern including a first plurality of rows of spaced-apart crossed-slot sterilant apertures and a second plurality of rows of spaced-apart crossed-slot sterilant apertures, wherein the aperture-to-aperture spacing in each row of said first plurality is substantially the same as the aperture-to-aperture spacing in each row of said second plurality and wherein the aperture locations in said second plurality are shifted relative to the aperture locations in said first plurality by a distance which is equal to approximately one-half of the aperture-to-aperture spacing; and
a plurality of integral holder panels which are constructed and arranged to receive said medical components and to assemble into said main panel by using selected ones of said plurality of crossed-slot sterilant apertures, each of said plurality of holder panels having a main body portion positioned on a first side of said main panel, an elongated base portion positioned on a second side of said main panel, said second side being oppositely positioned relative to said first side, and a web portion positioned between said main body portion and said elongated base portion, said web portion being captured by a corresponding one of said crossed-slot sterilant apertures, each elongated base portion including a plurality of spaced-apart insert ribs, the assembly of each holder panel of said plurality into said main panel being achieved by each of said plurality of spaced-apart insert ribs being inserted through a different one of said crossed-slot sterilant apertures.

8. The combination of claim 7 wherein said main body portion has a substantially flat lower surface and said elongated base portion has oppositely disposed upper edges, and wherein said main panel has a thickness which is substantially equal to the distance between the substantially flat surface of said main body portion and the upper edges of said elongated base portion.

9. The combination of claim 8 wherein said elongated base portion has a generally circular shape in lateral section.

10. The combination of claim 7 wherein each crossed-slot sterilant aperture of said plurality includes a first oblong slot having a first centerline axis and crossing at an approximate right angle therewith a second, substantially identical oblong slot having a second centerline axis, the first and second centerline axes intersecting at a geometric center of the corresponding aperture.

11. The combination of claim 7 wherein a first one of said plurality of spaced-apart insert ribs having an elongated length with a leading edge and a trailing edge and the next adjacent spaced-apart insert rib having a substantially equivalent elongated length with a leading edge and a trailing edge, wherein the trailing edge of said first insert rib is spaced apart from the leading edge of said next adjacent insert rib.

12. The combination of claim 11 wherein the length dimension from the leading edge of said first insert rib to the leading edge of said next adjacent insert rib is approximately equal to the aperture-to-aperture spacing within each row.

13. A combination comprising:
an autoclave tray for medical components which is arranged with a substantially planar main panel which defines a plurality of apertures, each aperture of said plurality having a first receiving slot of a first length and an intersecting second receiving slot of a second length, the intersection of said two slots defining an aperture center and wherein said plurality of apertures are disposed in a repeating four-corner diamond pattern; and
a plurality of integral holder panels which are constructed and arranged to receive said medical components and to assemble into said main panel by using selected ones of said plurality of apertures, each of said plurality of holder panels having a main body portion positioned on a first side of said main panel, an elongated base portion positioned on a second side of said main panel, said second side being oppositely positioned relative to said first side, and a web portion positioned between said main body portion and said elongated base portion, said web portion being captured by a corresponding one of said crossed-slot sterilant apertures, each elongated base portion including a plurality of spaced-apart insert ribs, the assembly of each holder panel of said plurality into said main panel being achieved by each of said plurality of spaced-apart insert ribs being inserted through a different one of said crossed-slot sterilant apertures.

14. A combination comprising:
an autoclave tray for medical components which is constructed and arranged with a plurality of crossed-slot sterilant apertures, each sterilant aperture being formed by two slots arranged substantially perpendicular to each other and having a geometric center and being disposed in a substantially uniform pattern of staggered rows with substantially uniform spacing between said geometric centers within each row and substantially uniform spacing between adjacent rows; and
a plurality of holder panels constructed and arranged to receive said medical components and to assemble into said tray by using selected ones of said plurality of sterilant apertures, each of said plurality of holder panels having an elongated insertable base portion and a main body portion, said elongated insertable base portion including a plurality of insertable sections wherein each insertable section is inserted into a different one of said plurality of crossed-slot sterilant apertures and each insertable section including an enlarged tang end whose lateral width is greater than the lateral width of either slot of said corresponding crossed-slot sterilant aperture.

15. A combination comprising:

an autoclave tray for medical components which is arranged with a plurality of crossed-slot sterilant apertures, said tray having a top surface and each sterilant aperture defining a bottom surface, each sterilant aperture further having a geometric center and being positioned in a substantially uniform pattern of staggered rows with substantially uniform spacing between said geometric centers with each row; and a plurality of holders which are constructed and arranged to (a) receive and retain one or more of said medical components and (b) assemble into said autoclave tray by using selected ones of said plurality of sterilant apertures, each holder of said plurality having a body portion positioned above said tray top surface, an enlarged tang portion positioned below said bottom surface and a web portion positioned between said top surface and said bottom surface, said tang portion constructed and arranged into a plurality of spaced-apart elongated tang sections, each of said plurality of elongated tang sections being inserted into a different one of said crossed-slot sterilant apertures.

16. The combination of claim 15 wherein each crossed-slot sterilant aperture of said plurality includes a first oblong slot having a first centerline axis and crossing at an approximate right angle therewith a second, substantially identical oblong slot having a second centerline axis, the first and second centerline axes intersecting at the geometric center of the corresponding sterilant aperture.

17. The combination of claim 16 wherein each elongated tang section has a length which is less than the length of said first oblong slot and which is also less than the length of said second oblong slot.

18. The combination of claim 17 wherein each of said plurality of spaced-apart elongated tang sections has a generally circular shape in lateral section, the lateral diameter width of each elongated tang section being larger than the lateral width of said first oblong slot and larger than the lateral width of said second oblong slot.

* * * * *

UNITED STATES PATENT AND TRADEMARK OFFICE
CERTIFICATE OF CORRECTION

PATENT NO.    : 5,441,709
DATED         : August 15, 1995
INVENTOR(S)   : Bernie B. Berry, Jr.

It is certified that error appears in the above-indentified patent and that said Letters Patent is hereby corrected as shown below:

Column 5, line 6, please change "to" to "for".

Column 6, line 61, please change "50=" to "50'".

Column 7, line 59, please change "lots" to "slots".

Signed and Sealed this

Nineteenth Day of December, 1995

*Attest:*

BRUCE LEHMAN

*Attesting Officer*         *Commissioner of Patents and Trademarks*